(12) United States Patent
Wang et al.

(10) Patent No.: US 11,191,447 B2
(45) Date of Patent: Dec. 7, 2021

(54) BREATH BY BREATH REASSESSMENT OF PATIENT LUNG PARAMETERS TO IMPROVE ESTIMATION PERFORMANCE

(71) Applicant: KONINKLIJKE PHILIPS N.V., Eindhoven (NL)

(72) Inventors: Dong Wang, Scarsdale, NY (US); Francesco Vicario, Boston, MA (US); Antonio Albanese, New York, NY (US); Nikolaos Karamolegkos, New York, NY (US); Nicolas Wadih Chbat, White Plains, NY (US); Limei Cheng, Irvine, CA (US)

(73) Assignee: Koninklijke Philips N.V., Eindhoven (NL)

( * ) Notice: Subject to any disclaimer, the term of this patent is extended or adjusted under 35 U.S.C. 154(b) by 843 days.

(21) Appl. No.: 15/772,982

(22) PCT Filed: Oct. 25, 2016

(86) PCT No.: PCT/IB2016/056392
§ 371 (c)(1),
(2) Date: May 2, 2018

(87) PCT Pub. No.: WO2017/077417
PCT Pub. Date: May 11, 2017

(65) Prior Publication Data
US 2018/0317808 A1  Nov. 8, 2018

Related U.S. Application Data

(60) Provisional application No. 62/249,647, filed on Nov. 2, 2015.

(51) Int. Cl.
*A61B 5/08*  (2006.01)
*A61B 5/00*  (2006.01)
(Continued)

(52) U.S. Cl.
CPC ........... *A61B 5/0816* (2013.01); *A61B 5/085* (2013.01); *A61B 5/4836* (2013.01);
(Continued)

(58) Field of Classification Search
None
See application file for complete search history.

(56) References Cited

U.S. PATENT DOCUMENTS

5,876,352 A   3/1999   Weismann
8,544,466 B2  10/2013  Blanch et al.
(Continued)

FOREIGN PATENT DOCUMENTS

WO   2010070498 A1   6/2010
WO   2016128846 A1   8/2016
WO   2016193915 A1   12/2016

OTHER PUBLICATIONS

Albanese: "Physiology-Based Mathematical Models for the Intensive Care Unit: Applicatio to Mechanical Ventilation"; Columbia University 2014, 242 pages.

*Primary Examiner* — Michael R Bloch
(74) *Attorney, Agent, or Firm* — Daniel H. Brean

(57) ABSTRACT

In respiratory monitoring, a breathing cycle detector (44) detects a breath interval in airway pressure and/or flow data. A respiratory parameters estimator and validator (30) asynchronously fits the airway pressure and airway flow data to an equation of motion of the lungs relating airway pressure and airway flow to generate asynchronously estimated respiratory parameters for the breath interval, using a sliding time window that is not synchronized with the breath interval. The asynchronously estimated respiratory parameters for the breath interval are validated using at least one physiological plausibility criterion defined with respect to the breath interval. Responsive to failure of the validation, the airway pressure and airway flow data are synchronously fitted to the
(Continued)

equation of motion of the lungs to generate synchronously estimated respiratory parameters for the breath interval. The synchronous fitting is performed in a time window aligned with the breath interval.

20 Claims, 3 Drawing Sheets

(51) Int. Cl.
    *A61B 5/085* (2006.01)
    *A61M 16/00* (2006.01)
    *G16H 50/20* (2018.01)

(52) U.S. Cl.
    CPC .......... *A61B 5/7221* (2013.01); *A61B 5/7242* (2013.01); *A61M 16/0051* (2013.01); *A61M 16/026* (2017.08); *G16H 50/20* (2018.01); *A61B 5/6867* (2013.01); *A61M 2016/0027* (2013.01); *A61M 2016/0036* (2013.01); *A61M 2230/40* (2013.01)

(56) References Cited

U.S. PATENT DOCUMENTS

| | | | |
|---|---|---|---|
| 8,960,192 B2 | 2/2015 | Welzien et al. | |
| 2003/0010339 A1* | 1/2003 | Banner | A61M 16/0051 128/204.18 |
| 2010/0071696 A1* | 3/2010 | Jafari | A61M 16/026 128/204.23 |
| 2010/0307499 A1* | 12/2010 | Eger | A61B 5/085 128/204.23 |
| 2014/0276173 A1* | 9/2014 | Banner | A61M 16/0833 600/533 |

* cited by examiner

BREATH BY BREATH REASSESSMENT OF PATIENT LUNG PARAMETERS TO IMPROVE ESTIMATION PERFORMANCE

CROSS-REFERENCE TO PRIOR APPLICATIONS

This application is the U.S. National Phase application under 35 U.S.C. § 371 of International Application No. PCT/IB2016/056392, filed on Oct. 25, 2016, which claims the benefit of U.S. Provisional Patent Application No. 62/249,647, filed on Nov. 2, 2015. These applications are hereby incorporated by reference herein.

FIELD

The following relates generally to the respiratory arts, respiratory monitoring arts, and related arts such as mechanical ventilation arts.

BACKGROUND

Clinical assessment of the respiratory system may be performed on a quantitative basis by estimating certain respiratory values, e.g. respiratory muscle pressure, respiratory system resistance, and respiratory system compliance or elastance.

The respiratory muscle pressure, typically denoted as $P_{mus}(t)$, is a (negative) pressure applied by the patient during respiration. More particularly, during inspiration the thoracic diaphragm operates to expand the volume of the thoracic cavity, thus reducing pressure for a given volume of air (as in the case of a blocked airway) or drawing air into the lungs (in the case of normal inhalation). Respiratory muscle pressure is a useful metric for respiratory monitoring generally as it is a metric of spontaneous breathing effort by the patient. Estimating $P_{mus}(t)$ is of particular value in conjunction with mechanical ventilation support modes such as Pressure Support Ventilation (PSV) in which the patient and the mechanical ventilator share the mechanical work performed on the respiratory system. Usually the goal is to provide minimal mechanical ventilation that is sufficient to achieve efficient respiration without fatiguing the patient. Quantitative assessment of $P_{mus}(t)$ can therefore be used to select the appropriate level of ventilation support delivered by the ventilator in order to prevent both atrophy and fatigue of patient respiratory muscles.

The clinical parameter commonly used to assess the effort made by the patient is known as Power of Breathing (PoB) or Work of Breathing (WoB). The PoB can be computed from an estimate of $P_{mus}(t)$ by integration, i.e.:

$$PoB = \frac{1}{T}\int_T P_{mus}(t)dV(t) \quad (1)$$

where T is some chosen time interval preferably encompassing several breaths and V(t) is the lung volume. PoB is measured in units of power or energy per unit time, e.g. Joules/minute. Work of breathing is similar, except the integration time interval T in Equation (1) is defined for WoB as a single breath (or the inspiratory period of a breath since $P_{mus}(t)=0$ may be assumed for expiration). WoB is thus in units of energy/breath, e.g. Joules/breath. One complication of WoB is that breath duration can in general vary from breath to breath.

The respiratory muscle pressure, $P_{mus}(t)$, may be measured invasively, for example by measuring the esophageal pressure ($P_{es}$) via insertion of a balloon-tipped catheter in the patient's esophagus. In this approach, the measured $P_{es}(t)$ is assumed to be a good proxy for the pleural pressure ($P_{pl}$) and can be used, in conjunction with an estimate of chest wall compliance $C_{rs}$ (or elastance $E_{rs}=1/C_{rs}$), to compute the WoB via the so-called Campbell diagram or, equivalently, via explicit computation of $P_{mus}(t)$ and then of WoB via Equation (1) with time interval T being one breath or inspiration period. Invasive measurement of $P_{mus}(t)$ can be problematic since placing the balloon to an appropriate position is a challenging task even for an experienced professional and inappropriate placement of the balloon makes the measured $P_{es}(t)$ data useless.

Respiratory system resistance ($R_{rs}$) and compliance ($C_{rs}$) or elastance ($E_{rs}$) provide quantitative information about the mechanical properties of the patient's respiratory system. These respiratory system values can be used to diagnose respiratory diseases and/or to inform selection of appropriate mechanical ventilation modalities and/or therapeutic paths. Estimation of respiratory system resistance and compliance (or elastance) can be performed by applying the flow-interrupter technique (also called End Inspiratory Pause, EIP). However, this interferes with the therapeutic mechanical ventilation pattern that provides life-sustaining respiration to the patient.

The following discloses a new and improved system and method that addresses the above referenced issues, and others.

SUMMARY

In one disclosed aspect, a respiratory monitor device includes an airway pressure sensor configured to acquire airway pressure data as a function of time and an airway flow sensor configured to acquire airway flow data as a function of time. A breathing cycle detector comprises an electronic processor programmed to detect a breath interval bounded by successive start of inspiration (SOI) events in at least one of the airway pressure data and the airway flow data. A respiratory parameters estimator and validator comprises an electronic processor programmed to perform operations including: asynchronously fitting the airway pressure and airway flow data to an equation of motion of the lungs relating airway pressure and airway flow to generate asynchronously estimated respiratory parameters for the breath interval, the asynchronous fitting being performed in multiple sliding time windows that are not synchronized with the breath interval; performing validation of the asynchronously estimated respiratory parameters for the breath interval using at least one physiological plausibility criterion defined with respect to the breath interval; and responsive to failure of the validation of the asynchronously estimated respiratory parameters for the breath interval, synchronously fitting the airway pressure and airway flow data to the equation of motion of the lungs to generate synchronously estimated respiratory parameters for the breath interval, the synchronous fitting being performed in a time window aligned with the breath interval.

In another disclosed aspect, a non-transitory storage medium stores instructions executable by an electronic processor to perform a respiratory parameters estimation method operating on airway pressure data and airway flow data. The method includes: detecting a breath interval bounded by successive start of inspiration (SOI) events in at least one of the airway pressure data and the airway flow data; fitting the airway pressure and airway flow data to an equation of motion of the lungs relating airway pressure and airway flow to generate estimated respiratory parameters for the breath interval, the fitting being performed using one of (1) multiple sliding time windows that are not synchronized with the breath interval and (2) a single-breath parameterized respiratory muscle pressure profile (80, 82) that is aligned with the SOI of the breath interval; performing validation of the estimated respiratory parameters for the breath interval using at least one physiological plausibility criterion defined with respect to the breath interval; and responsive to failure of the validation of the estimated respiratory parameters for the breath interval, re-fitting the airway pressure and airway flow data to the equation of motion of the lungs to generate re-estimated respiratory parameters for the breath interval using the other of (1) the multiple sliding time windows that are not synchronized with the breath interval and (2) the single-breath parameterized respiratory muscle pressure profile that is aligned with the SOI of the breath interval.

In another disclosed aspect, a respiratory parameters estimation method operates on airway pressure data and airway flow data. The respiratory parameters estimation method comprises: detecting a breath interval bounded by successive start of inspiration (SOI) events in at least one of the airway pressure data and airway flow data; fitting the airway pressure and airway flow data to an equation of motion of the lungs relating airway pressure and airway flow to generate estimated respiratory parameters for the breath interval, the fitting being performed using one of (1) asynchronous fitting in a sliding time windows that is not synchronized with the breath interval and (2) synchronized fitting in a time window equal to the breath interval; validating the estimated respiratory parameters for the breath interval; and responsive to a failure of the validating, re-fitting the airway pressure and airway flow data to the equation of motion of the lungs to generate re-estimated respiratory parameters for the breath interval using the other of (1) asynchronous fitting in a sliding time window that is not synchronized with the breath interval and (2) synchronized fitting in a time window equal to the breath interval.

One advantage resides in providing non-invasive estimation of respiratory effort.

Another advantage resides in providing non-invasive estimation of respiratory effort that balances efficient quasi-instantaneous respiratory data analysis with physiological "first principles" information obtainable from the respiratory cycle.

Another advantage resides in providing non-invasive Work of Breathing (WoB) or Power of Breathing (PoB) estimates for a spontaneously breathing patient with improved accuracy for use in setting an appropriate level of mechanical ventilation support.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 4 also indicates two successive positions of the sliding window of the sliding time window estimator of FIG. 2.

DETAILED DESCRIPTION

Figure 1:
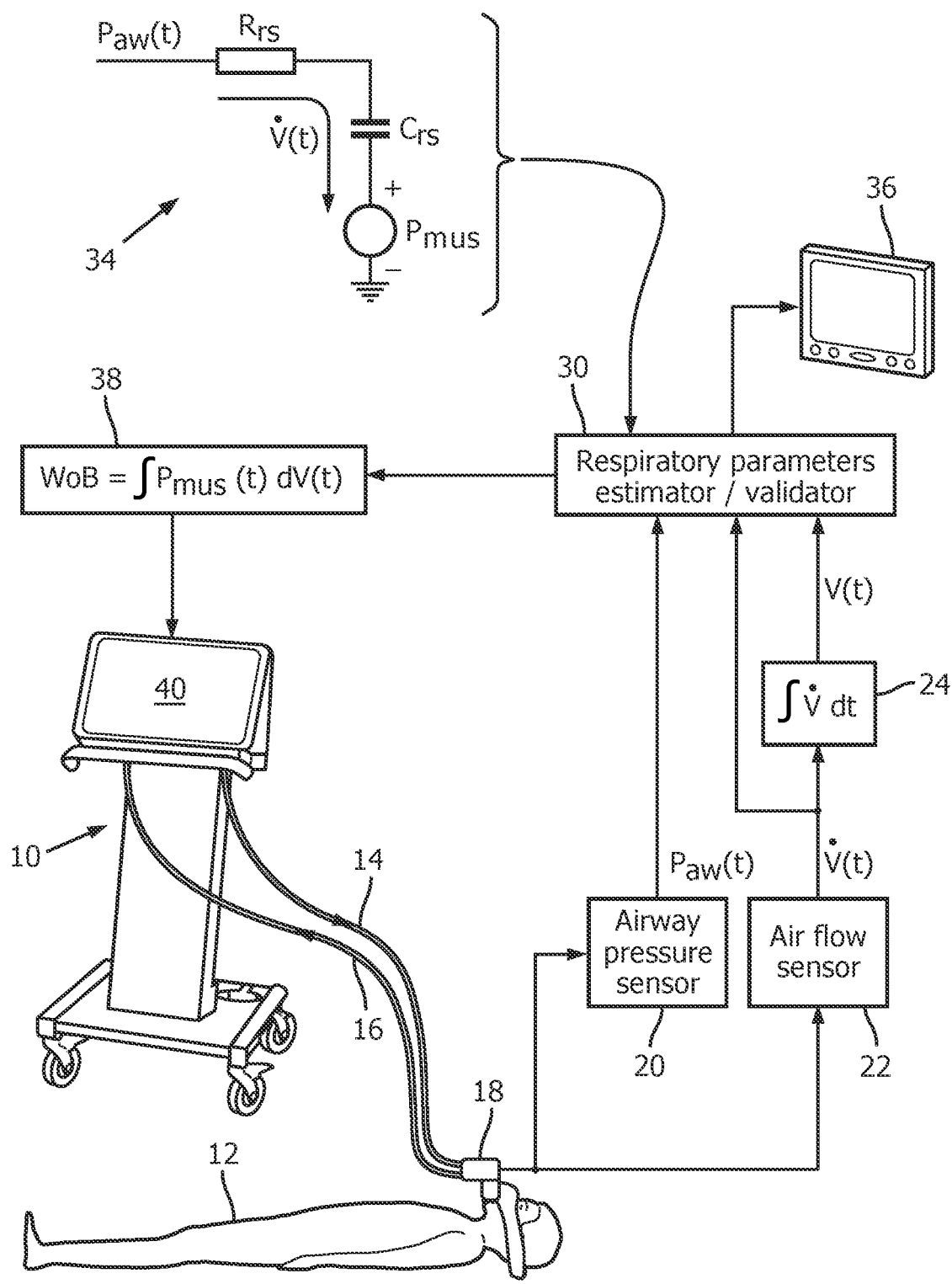
FIG. 1 diagrammatically illustrates a respiratory parameters estimation system in combination with illustrative applications thereof including a patient monitor and a mechanical ventilator.

In approaches disclosed herein, the respiratory muscle pressure $P_{mus}(t)$, respiratory system resistance $R_{rs}$, and respiratory system compliance $C_{rs}$ or elastance $E_{rs}=1/C_{rs}$ are simultaneously estimated by evaluating the Equation of Motion of the Lungs:

$$P_{aw}(t) = R_{rs}\dot{V}(t) + \left(\frac{1}{C_{rs}}\right)V(t) + P_{mus}(t) + P_{baseline} \text{ or} \quad (2)$$

$$P_{aw}(t) = R_{rs}\dot{V}(t) + E_{rs}V(t) + P_{mus}(t) + P_{baseline}$$

where $P_{aw}(t)$ is the measured airway pressure, $\dot{V}(t)$ is the measured airway flow, $V(t)$ is the respired air volume, i.e. $V(t)=\int\dot{V}(t)dt$, and $P_{baseline}$ is a constant. The two versions of the Equation of Motion of the Lungs presented in Equation (2) differ only by the substitution of the term $$\left(\frac{1}{C_{rs}}\right)$$

including respiratory compliance $C_{rs}$ by respiratory elastance $E_{rs}$ using the inverse relationship $$\left(\frac{1}{C_{rs}}\right) = E_{rs}.$$

In performing simultaneous estimation using Equation (2), the airway pressure $P_{aw}(t)$ and airway flow $\dot{V}(t)$ are sampled. Evaluating N samples entails solving for N+2 unknowns (including N values of $P_{mus}(t)$ and the values of $R_{rs}$ and $C_{rs}$). This is an underdetermined problem as the number of data points (N) is less than the number of unknowns (N+2).

One approach employed herein to solve this underdetermined problem is to fit Equation (2) within a sliding window. By choosing the window to be of sufficiently small width, the respiratory muscle pressure $P_{mus}(t)$ may be approximated by a low-order polynomial, e.g. a zero-order polynomial (i.e. a constant value), a first-order polynomial (linear approximation), or a second-order polynomial (parabolic approximation). The optimal choice of polynomial order depends upon the position of the sliding window within the breath cycle—but this may be difficult to determine, especially in the case of a patient on a mechanical respiratory having poor synchrony between the patient and ventilator. Accordingly, in approaches disclosed herein the data within the window are fitted using each of the different-order polynomial approximations (e.g. zeroth, first, and second) and the best fit is used. This class of approaches is referred to herein as asynchronous sliding window respiratory parameters estimation (where "asynchronous" indicates that the time duration and movement of the sliding window are not synchronized with the breathing cycle).

Another approach employed herein to solve this underdetermined problem is to fit Equation (2) on a per-breath basis, using a model for $P_{mus}(t)$ that takes into account its expected single-breath profile as represented by a single-breath parameterized respiratory muscle pressure profile denoted herein as $P_{mus,profile}$. This approach is synchronized with the breathing cycle and advantageously makes use of physiological knowledge of the expected $P_{mus}(t)$ waveform. However, it relies upon accurate segmentation of the respiratory data into distinct breaths, and further makes assumptions about the $P_{mus}(t)$ waveform which might vary for different patients. To some degree, the latter difficulty can be overcome by repeating the fitting of Equation (2) to a single-breath using two (or more) different profiles to better capture the specific shape of $P_{mus}(t)$ for s given patient. This class of approaches is referred to herein as synchronous or per-breath respiratory parameters estimation (where "synchronous" indicates that the estimation is synchronized with the breathing cycle by being performed on a per-breath basis, i.e. the fitting window is aligned with a breath interval, and in the illustrative embodiments the synchronous fitting window equals the breath interval).

The inventors have performed extensive tests of both the asynchronous sliding window estimation approaches and the per-breath estimation approaches with animal and human respiratory data, and have found that each approach has its own extreme cases in which its respiratory estimation is not accurate. For example, while asynchronous sliding window estimation approaches was found to work well in many cases, inaccuracies arose in the case of a subject on mechanical ventilation using the pressure support ventilation (PSV) mode with a high pressure setting (e.g. with a PSV level of 20 cmH$_2$O). Indeed, with high-setting PSV ventilation the $P_{mus}(t)$ estimated by asynchronous respiratory parameters estimation was sometimes found to assume positive excursions over portions of the breathing cycle, in which the fitted value goes to higher (positive) pressure than the baseline value. These positive respiratory muscle pressure excursions are physiologically unrealistic since the muscle pressure operating via the thoracic diaphragm expands the lungs, generating a lung volume increase and consequent negative pressure.

By contrast, in the case of synchronous or per-breath respiratory parameters estimation inaccuracies arose in the case of a subject on mechanical ventilation using the pressure support ventilation (PSV) mode with a low pressure setting. In this case the ventilator pressure support usually terminates before the end of the patient inhalation effort. The inaccuracy is most severe with no ventilator support (effectively PSV pressure setting of zero), since in this case there is no externally applied airway pressure and the problem becomes ill-posed.

It is recognized herein that these difficulties can be overcome by combining the asynchronous and synchronous respiratory parameters estimation methods. In illustrative embodiments, the asynchronous respiratory parameters estimation method is used as the primary estimation method since it is essentially a real-time continuous technique operating with a temporal latency on the order of the width of the sliding time window. However, output of this data is delayed until each breath is complete and its corresponding asynchronously estimated parameter values are validated to ensure they are physiologically plausible. If not, then synchronous, i.e. per-breath estimation is applied on the data for the just-completed breath. This approach accepts the inherent one-breath latency of the per-breath method. Due to the few fitted parameters of the per-breath approach, it is fast and the per-breath optimization can be completed quickly, e.g. well within the time interval of the next breath. If the synchronous per-breath respiratory parameter estimation validates (i.e. provides physiologically plausible values) then the results of the per-breath estimation are used instead of the asynchronous estimation. If the per-breath estimation also fails to validate, then various remedial actions can be taken, such as attempting another fit assuming $P_{mus}(t)=0$ or generating an alarm (while optionally re-using the last valid breath data). The option of performing a further fit with $P_{mus}(t)=0$ assumed is motivated by the recognition that both asynchronous and per-breath estimations are likely to fail under this limiting state, and additionally $P_{mus}(t)=0$ is a plausible physiological occurrence, indicating complete loss of spontaneous respiration, which is important to accurately detect.

To facilitate validation of the asynchronously estimated respiratory parameters on a per-breath basis, a latency of at least one breath is preferably introduced between the airway pressure and flow data acquisition and the output of $P_{mus}(t)$ and respiratory system parameters. This delay is inherent for the Work of Breathing or Power of Breathing calculation and generally acceptable for purposes such as displaying trend lines of these parameters, and/or controlling a mechanical ventilator using the $P_{mus}(t)$ estimation (or a time-integrated version such as Work of Breathing or Power of Breathing) as a control input.

With reference now to FIG. 1, a respiratory parameters estimation system employing the above principles is described, in combination with illustrative patient monitor and mechanical ventilator setting applications thereof. A mechanical ventilator 10 is providing mechanical ventilation of a patient 12 in a support mode, such as Pressure Support Ventilation (PSV), in which the patient 12 may be spontaneously breathing. The mechanical ventilator 10 delivers pressurized air to the patient via an inlet air hose 14 and expired air returns to the ventilator 10 via an outlet air hose 16. Coupling of air to and from the patient is via a suitable patient accessory 18, such as a full-face mask or a tracheal tube.

As diagrammatically indicated in FIG. 1, the air flow circuit includes an airway pressure sensor 20 that measures (i.e. samples) the airway pressure $P_{aw}(t)$, and an airway flow sensor 22 that measures the airway flow $\dot{V}/(t)$. An integrator 24 computes the air volume $V(t)=\int(t)dt$. A respiratory parameters estimator/validator 30 evaluates Equation (2) or another suitable Equation of Motion of the Lungs using a processing sequence such as that described later herein with reference to FIG. 2 in order to determine the respiratory muscle pressure $P_{mus}(t)$ over each breath interval and the respiratory system resistance $R_{rs}$ and compliance $C_{rs}$ or elastance $E_{rs}$. For illustration, an equivalent respiratory circuit 34 of Equation (3) is diagrammatically shown in FIG. 1. The computed respiratory muscle pressure, resistance, and compliance or elastance values may be variously used, for example displayed on the patient or nurses' station monitor 36, and/or processed by a WoB calculator 38 (or alternatively a PoB calculator) in accordance with Equation (1), or so forth. The calculated PoB or WoB may be displayed on a display component 40 of the mechanical ventilator 10, e.g. as a trend line and/or as a current numerical value, for reference by the physician in assessing and optionally adjusting the ventilator setting(s). Automated closed-loop control of these settings based on the calculated PoB or WoB (and possibly other inputs) is also contemplated.

The data acquisition and processing components 20, 22, 24, 30, 38 may be variously arranged in a specific implementation. For example, the airway pressure sensor 20 may be built into the patient accessory 18, while the airway flow sensor 22 may be built into the patient accessory 18 or mounted on one of the air hoses 14, 16 or housed within the mechanical ventilator 10. The data analysis components 24, 30, 32 may be implemented by any electronic data processing device, such as a microcontroller or microprocessor or other electronic processor of the mechanical ventilator 10, and/or a microprocessor or microcontroller or other electronic processor of the patient or nurses' station monitor 36, or so forth. The data processing may be further embodied as a non-transitory storage medium storing instructions readable and executable by an electronic processor to perform the disclosed data processing and other functions (e.g. data acquisition, display device control, et cetera). The non-transitory storage medium may, for example, including a hard disk drive or other magnetic storage medium, and/or an optical disk or other optical storage medium, and/or a flash memory or other electronic storage medium, and/or so forth. To enable electronic data processing of the acquired $P_{aw}(t)$ and $\dot{V}(t)$, these signals are sampled and digitized. The sampling and analog-to-digital (A/D) conversion circuitry may be built into the respective sensors 20, 22, or may be performed by sampling and A/D converters associated with sensor input ports of the mechanical ventilator 10 or patient or nurses' station monitor 26, or so forth—these data acquisition and pre-processing or data formatting details are not illustrated in diagrammatic FIG. 1.

Figure 2:
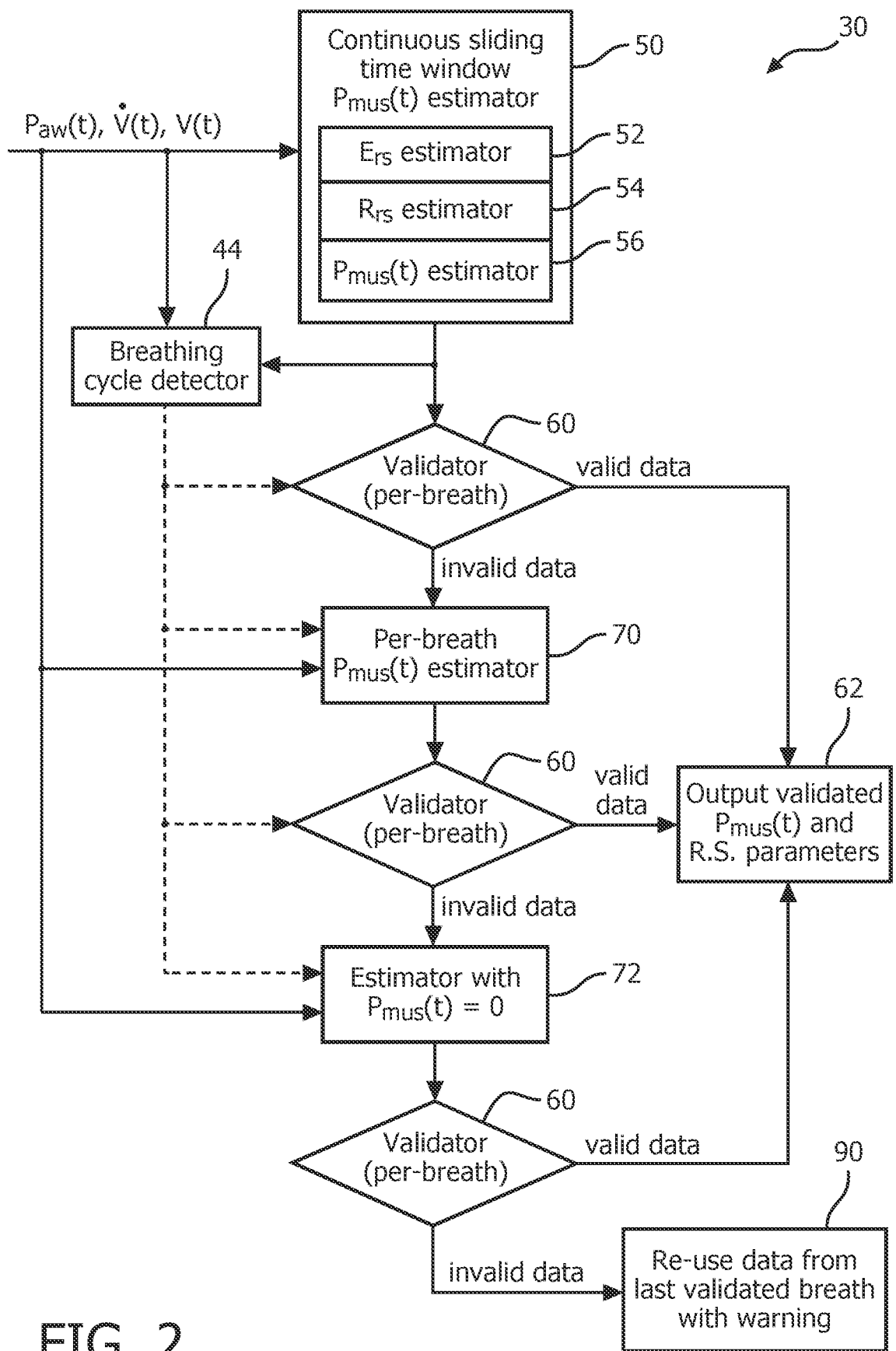
FIG. 2 shows a block diagram of an illustrative implementation of the respiratory parameters estimator/validator of the system of FIG. 1.

With reference now to FIG. 2, a block diagram of an illustrative implementation of the respiratory parameters estimator/validator 30 of FIG. 1 is described. The respiratory parameters estimator/validator 30 receives as input the airway pressure $P_{aw}(t)$ measured by the airway pressure sensor 20, the airway air flow $\dot{V}(t)$ measured by the air flow sensor 22, and the air volume $V(t)$ computed by the integrator 24 integrating the air flow $\dot{V}(t)$. The validation of the estimated respiratory parameters assesses the physiological plausibility of the estimates for this purpose, it is generally useful to identify the start of inspiration (SOI) and, optionally, the start of expiration (SOE) for each breath. (It will be appreciated that, neglecting any brief pauses, the SOI also demarcates the end of the previous expiration period; and likewise the SOE also demarcates the end of the previous inspiration period). To this end, a breathing cycle detector 44 is configured to segment the acquired ($P_{aw}(t)$, $\dot{V}(t)$, $V(t)$) sample stream into time segments corresponding to inspiration periods each starting with a SOI and ending with a SOE, and expiration periods each starting with an SOE and ending with an SOI. The SOI may, for example, be detected by analyzing the airway pressure samples $P_{aw}(t)$ and may, by way of illustration, detect the SOI as a characteristic abrupt decrease in $P_{aw}(t)$ indicating the beginning of the intake of a breath. Alternatively, SOI may be detected from the air flow data $\dot{V}(t)$, i.e. with SOI being indicated by a rapid increase in air flow $\dot{V}(t)$. Each successive breath is then defined as the interval from the onset of one inspiration period to the onset of the next inspiration period. Within each breath, the SOE can optionally be detected, for example as the point where the lung volume $V(t)$ reaches a maximum value. In some embodiments, the breathing cycle detector 44 may leverage the respiratory parameter estimates output by the first estimation stage, that is, by an illustrative asynchronous sliding time window respiratory parameters estimator 50 to be described next, in order to identify SOI and SOE. In this approach, the SOI may be considered to be the point at which $P_{mus}(t)$ inflects downward to assume a negative slope (i.e. $P_{mus}(t)$ trends toward more negative values). The SOE may be considered as the point in time in which $P_{mus}(t)$ returns to a flat, i.e. baseline, value indicating termination of respiratory effort by the patient. For this approach to work, the respiratory estimates output by the asynchronous sliding time window respiratory parameters estimator 50 must be accurate enough to produce reasonable SOI (and optionally also SOE) estimates. Since this may not be the case (which is why these estimates are validated based in part on the SOI and SOE estimates), they may be used as secondary information, e.g. to adjust the SOI and SOE values generated from the airway pressure analysis.

With continuing reference to FIG. 1, some illustrative embodiments of the asynchronous sliding time window respiratory parameters estimator 50 are now described. It is to be appreciated that the asynchronous sliding time window respiratory parameters estimator 50 is not synchronized with the respiration, that is, does not rely upon the SOI or SOE output by the breathing cycle detector 44, but rather performs respiratory parameters estimation on an asynchronous basis without reference to the breathing cycle (although the breathing cycle is expected to be "re-constructed" in the output by the asynchronously estimated respiratory muscle pressure $P_{mus}(t)$). In general, the time duration of the sliding time window used in the asynchronous estimation is fixed and is not aligned with any particular time interval of the breathing cycle (which, when driven by spontaneous breathing, is not a fixed time interval as it may vary from breath to breath), and the movement of the sliding time window is not synchronized with the breathing cycle. The asynchronous sliding time window respiratory parameters estimator 50 evaluates the Equation of Motion of the Lungs (Equation (2)) using least squares estimation applied in a sliding or moving time window applied to the airway measurements ($P_{aw}(t)$, $\dot{V}(t)$, $V(t)$) To overcome the underdetermined nature of Equation (2), the asynchronous sliding window respiratory parameters estimator 50 uses successive estimation of: (1) the elastance or compliance ($E_{rs}$ or $C_{rs}$) parameter via an $E_{rs}$ estimator 52; followed by (2) estimation of the resistance ($R_{rs}$) parameter via an $R_{rs}$ estimator 54; followed by (3) estimation of the respiratory muscle pressure ($P_{mus}(t)$) parameter via a $P_{mus}(t)$ estimator 56. These successive estimators 52, 54, 56 are applied within a time window which is generally of duration two seconds or less, and more preferably of duration one second or less, and in an illustrative example of duration 0.6 seconds with data sampling at 100 Hz so that the time window contains 60 samples. An upper limit on the duration of the time window is imposed by the respiration rate, which for a normal adult is typically 12 to 20 breaths per minute corresponding to a breathing cycle of duration 3-5 seconds. The duration of the time window is preferably a fraction of the breathing cycle duration so that the parameters $E_{rs}$ and $R_{rs}$ can be reasonably assumed to be constant within each time window, and variation of $P_{mus}(t)$ within each time window can be represented using a relatively simple approximation function (e.g. a low-order polynomial in the illustrative examples disclosed herein). The estimators 52, 54, 56 are successively applied within each time window, and for each successive (and partially overlapping) time interval (hence the term "moving" or "sliding" time window), to provide estimation of $E_{rs}$, $R_{rs}$, and $P_{mus}(t)$ in real time. In the illustrative examples, the values of $E_{rs}$ and $R_{rs}$ are assumed to be constant within each time window, so that the estimation of these parameters is in real-time with a time resolution comparable to the duration of the time window, e.g. two second or less in some embodiments, or more preferably one second or less, and 0.6 seconds in the illustrative examples. If successive time windows partially overlap, this can further improve the effective time resolution. The real-time estimation of $P_{mus}(t)$ can be of higher temporal resolution than $E_{rs}$ and $R_{rs}$, since $P_{mus}(t)$ is calculated based on the Equation of the motion of the Lungs and the estimated $E_{rs}$ and $R_{rs}$. Furthermore, some filters (e.g. Kalman filters) can be used within the estimator 52, 54, 56 to improve the continuous estimation of $E_{rs}$, $R_{rs}$ from the sliding time window estimator.

The ordering of the estimators 52, 54, 56 in the illustrative asynchronous sliding window respiratory parameters estimator 50 is chosen based on the expectation that the elastance/compliance ($E_{rs}$ or $C_{rs}$) generally varies most slowly over time (being associated with the time-integrated air volume $V(t)$), the resistance $R_{rs}$ varies next most slowly, while $P_{mus}(t)$ varies most rapidly as it cycles over each inspiration period. However, it is contemplated to use different orderings, such as reversing the order of the estimators 52, 54. The illustrative examples employ a low-order approximation polynomial function for $P_{mus}(t)$. Instead of a low-order polynomial approximation, in other contemplated embodiments some other parameterized function of time is contemplated, such as a spline function.

In the following, some illustrative embodiments of the estimators 52, 54, 56 are described.

In the first pass performed by the $E_{rs}$ estimator 52), all three parameters $E_{rs}$, $R_{rs}$, and $P_{mus}(t)$ are assumed to be constant over the time window 130 and are computed simultaneously—but only the estimated $\hat{E}_{rs}$ is retained from this first pass. (In notation used herein, the overscript "hat", i.e. $\hat{p}$, is used to indicate the estimated value of parameter p.) In a second pass performed by the $R_{rs}$ estimator 54, the contribution of the now known (estimated) $\hat{E}_{rs}$ is removed by subtraction, and the remaining portion of the Equation of Lung Motion (Equation (2)) is fitted for $R_{rs}$ and $P_{mus}(t)$, the latter being approximated using a low order polynomial (n=0, 1, or 2). In experiments, it was found that the best choice of polynomial order is dependent upon the respiratory phase at which the time window is located due to possible overfitting—as respiratory phase is not known a priori in the estimation performed by the asynchronous estimator 50, in illustrative embodiments disclosed herein a weighted combination of polynomials of zeroeth, first, and second order is used. The output of the $R_{rs}$ estimator 54 is the estimated value of the respiratory resistance, i.e. $\hat{R}_{rs}$. Finally, in a third pass performed by the $P_{mus}(t)$ estimator 56, the contribution of the now known (estimated) $\hat{R}_{rs}$ is removed by further subtraction, and the remaining portion of the Equation of Lung Motion is directly fitted to obtain the estimated respiratory muscle pressure, i.e. $\hat{P}_{mus}(t)$.

In the illustrative $E_{rs}$ estimator 52, a difference operation is performed on the airway pressure $P_{aw}(t)$ and the output $\Delta P_{aw}(t)$ is calculated as $\Delta P_{aw}(t)=P_{aw}(t)-P_{aw}(t-1)$. A sliding window respiratory parameters estimator is used to estimate $E_{rs}(t)$—which is the respiratory system's elastance—based on the following difference equation:

$$\Delta P_{aw}(t) \approx R_{rs}\Delta \dot{V}(t)+E_{rs}\Delta V(t)+P_{mus} \qquad (3)$$

In the difference signal of Equation (3), the constant $P_{baseline}$ is canceled out. Equation (3) assumes that the parameters $E_{rs}$, $R_{rs}$, and $\Delta P_{mus}$ are constants over the time window (which, again, has a duration that is a fraction of a single breath). In the $E_{rs}$ estimator 52, these three parameters are jointly estimated using a least squares minimization. However, for the $E_{rs}$ estimator 52, only the estimate of $E_{rs}$, namely $\hat{E}_{rs}$, is used, while the other estimation outputs are discarded. The estimate $\hat{E}_{rs}$ computed by the $E_{rs}$ estimator 52 is a constant for a given position of the sliding time window; as $\hat{E}_{rs}$ is computed by the $E_{rs}$ estimator 52 for successive time windows, a time function $\hat{E}_{rs}(t)$ is developed. In some embodiments, the estimate $\hat{E}_{rs}(t)$ is filtered by a Kalman filter or another noise-suppressing filter in order to reduce noise.

The output $\hat{E}_{rs}(t)$ of the $E_{rs}$ estimator 52 is utilized by the succeeding $R_{rs}$ estimator 54 in performing the $R_{rs}$ estimation. For the $R_{rs}$ estimation 54, the elastic pressure component $E_{rs}V(t)$ of the Equation of Motion of the Lungs (Equation (2)) is cancelled out of $P_{aw}(t)$ using the estimate $\hat{E}_{rs}(t)$. This $E_{rs}$ cancellation operation can be expressed as:

$$\tilde{P}_{aw}(t)=P_{aw}(t)-\hat{E}_{rs}(t)V(t) \qquad (4)$$

Since $\hat{E}_{rs}(t)$ is the output of the $E_{rs}$ estimator 52, all terms of Equation (4) are either measured data or have known values. Inserting Equation (4) into Equation (2) with $E_{rs}=\hat{E}_{rs}(t)$ (that is, assuming that the estimate $\hat{E}_{rs}(t)$ output by the $E_{rs}$ estimator 52 is exactly correct) yields:

$$\tilde{P}_{aw}(t) \approx R_{rs}\dot{V}(t)+[P_{mus}(t)+P_{baseline}] \qquad (5)$$

Equation (5) is evaluated in the least squares sense over the time window using a polynomial representation of $[P_{mus}(t)+P_{baseline}]$ which is of order n where n=0 (zeroeth order; constant), n=1 (first order; linear), or n=2 (second order; quadratic). This leaves n+2 parameters to be fitted: the n+1 parameters of the polynomial representing $[P_{mus}(t)+P_{baseline}]$ and the $R_{rs}$ parameter. As there are no more than four parameters being fitted, the least squares optimization is fast, and it is feasible (in a time frame much less than a single breath) to repeat it for each of the zeroeth, first, and second order polynomials and to select the best fit. This is advantageous because $[P_{mus}(t)+P_{baseline}]$ may have a generally flat, linear, or curved shape depending upon where the time window is within the breath cycle, which is undetermined in the case of the asynchronous estimator 50. More particularly, $[P_{mus}(t)+P_{baseline}]$ is expected to be flat during the exhalation phase (no respiratory muscle pressure being applied), and is expected to be approximately linear during portions of the inhalation phase with curved (i.e. approximately quadratic) shape at transitions. These various possibilities can be accommodated (without knowing the respiratory phase) by performing the fit for n=0, n=1, and n=2 and taking the best fit result.

Although the least squares optimization of Equation (5) yields an estimate $R_{rs}$ for $R_{rs}$ as well as estimates for the one-to-three low-order polynomial parameters representing $[P_{mus}(t)+P_{baseline}]$, only the respiratory resistance estimate $\hat{R}_{rs}$ is retained as the output of the $R_{rs}$ estimator 54, while the estimates of the low-order polynomial parameters are discarded. A Kalman filter or other noise-suppressing filter may be applied to the function $\hat{R}_{rs}(t)$ generated by applying the $R_{rs}$ estimator 54 in successive (moving or sliding) time windows.

Finally, the $P_{mus}(t)$ estimator 56 is applied to estimate $P_{mus}(t)$. This estimation can be computed analytically in the time window using Equation (2) with $E_{rs}=\hat{E}_{rs}$ (from the $E_{rs}$ estimator 52 applied in the time window) and $R_{rs}=\hat{R}_{rs}$ (from the $R_{rs}$ estimator 54 applied in the time window), that is:

$$\hat{P}_{mus}(t)+P_{baseline}=P_{aw}(t)-\hat{R}_{rs}\dot{V}(t)-\hat{E}_{rs}V(t) \qquad (6)$$

The constant term $P_{baseline}$ could be removed on the physiological basis that $P_{mus}(t)$ must have a baseline value of zero over the expiration period; however, since it is often the waveform shape that is of most interest, in the following the respiratory muscle pressure is taken as the value with the possibly non-zero offset $P_{baseline}$ In other words, the "effective" respiratory muscle pressure is taken herein as the value $[P_{mus}(t)+P_{baseline}]$. A Kalman filter or other noise-suppressing filter may be applied to the function $P_{mus}(t)$.

It is to be appreciated that the asynchronous respiratory parameters estimation may employ other approaches for asynchronous estimation of the parameters within the sliding window besides the one described with reference to the cascaded estimators 52, 54, 56 in order to provide an estimate of $P_{mus}(t)$ and the respiratory system parameters within the time window without reference to the breathing phase. For example, as previously noted the order of the estimators 52, 54 may be reversed. In another contemplated variant approach the fitting is performed using a single least squares optimization that fits all of $R_{rs}$, $E_{rs}$ (or $C_{rs}$), and the n+1 parameters of a low-order polynomial approximation of $P_{mus}(t)$ (effectively combining the estimators 52, 54 into a single least squares optimization), and only the estimates for $R_{rs}$ and $E_{rs}$ are retained for input to the estimator 56.

In describing the component estimators 52, 54, 56 of the illustrative asynchronous sliding time window respiratory parameters estimator 50 to, the overscript "hat" notation i.e. $\hat{p}$, has been used to indicate the estimated value of parameter p. For convenience of notation hereinafter, the parameter estimates output by the asynchronous sliding time window respiratory parameters estimator 50 are represented without the "hat" notation, i.e. the estimates output by the asynchronous sliding time window respiratory parameters estimator 50 are indicated as the estimated respiratory muscle pressure $P_{mus}(t)$ and the estimated respiratory system parameters including estimated respiratory system resistance $R_{rs}(t)$ and estimated respiratory system elastance $E_{rs}(t)$ or compliance $C_{rs}(t)$.

With continuing reference to FIG. 2, the resulting parameter values $P_{mus}(t)$, $R_{rs}(t)$, and $E_{rs}(t)$ or $C_{rs}(t)$ are evaluated as to physiological plausibility by a validator 60 which operates on a per-breath basis using the SOI delineations detected by the breathing cycle detector 44, and in the illustrative embodiment also using the SOE delineations detected by the breathing cycle detector 44. The validator 60 quantitatively assesses physiological plausibility on the estimated respiratory muscle pressure $P_{mus}(t)$ over a current breath interval n which starts at data point SOI(n) and ends at data point SOI (n+1)−1 (or, alternatively, the "−1" may be omitted since the breathing cycle detector 44 generally has uncertainty of at least one data point), and optionally also quantitatively assesses physiological plausibility on the estimated respiratory system parameters.

Considering first $P_{mus}(t)$ (or, more precisely, $[\hat{P}_{mus}(t)+P_{baseline}]$), a physiologically plausible respiratory muscle pressure waveform for a normal breath in which the patient is contributing some effort should go negative from its nominal "zero" level ($P_{baseline}$) in the inhalation phase and should go back to its nominal "zero" level around the SOE point and stay at the nominal "zero" level in the exhalation phase. On this basis, and assuming that the SOI and SOE are known from the breathing cycle detector 44 as already described, the following illustrative two validity (i.e. physiological plausibility) criteria can be defined (where n denotes a current breath being analyzed for validity).

The first validity criterion is:

$$\text{mean}(P_{mus}(\text{SOI}(n):\text{SOE}(n))) < \text{mean}(P_{mus}(\text{SOE}(n)+d): \text{SOI}(n+1)-1)+a \quad (C1)$$

where the validation criterion C1 is met (valid) if the inequality holds. Validity criterion C1 requires that the mean of the estimated $P_{mus}(t)$ in the inhalation phase running from SOI(n) to SOE(n) should be less than its nominal "zero" level, which is approximated by the mean of the estimated $P_{mus}(t)$ over the exhalation phase. The constant d is a positive offset (d>0) that shifts the start of the region over which the mean is taken slightly away SOE(n) so as to avoid potential instability of the respiratory muscle pressure around SOE and to compensate for any error in the value of SOE detected by the breathing cycle detector 44. The endpoint SOI(n+1)−1 is the end-of-exhalation for the current breath n which is the data point just prior to the start of inhalation of the next breath SOI(n+1). The constant a is an optional design adjustment to improve robustness.

The second validity criterion is:

$$\text{abs}(\text{mean}(P_{mus}(\text{SOE}(n):\text{SOE}(n)+c)))-\text{mean}(P_{mus}(\text{SOE}(n)+d):\text{SOI}(n+1)-1) < b \quad (C2)$$

Validation criterion C2 requires that the mean of the estimated $P_{mus}(t)$ in a small time window around SOE(n) (the value with in the abs( . . . ) operation) should be close to its nominal "zero" level, which again is approximated by mean($P_{mus}$(SOE(n)+d):SOI(n+1)). The design parameter b is a constant that defines the maximum allowed offset.

The validator 60 applies both physiological plausibility criteria C1 and C2 and validates the respiratory parameters estimation if both criteria C1 and C2 are satisfied. It is noted that the physiological plausibility criteria C1 and C2 are merely illustrative examples, and other physiological plausibility criteria are contemplated, which are suitably defined based on the physiological knowledge of lung mechanics and the respiratory muscle pressure. In more general terms, the illustrative physiological plausibility criterion C1 compares the respiratory muscle pressure during inspiration to respiratory muscle pressure during expiration, while the illustrative physiological plausibility criterion C2 compares the respiratory muscle pressure at SOE to the respiratory muscle pressure during expiration. In some embodiments, further physiological plausibility criteria are applied that operate on the values of the respiratory parameters $R_{rs}$ and $E_{rs}$ (or C) for example, these values may be determined to be invalid if they are negative, or more stringent physiological plausibility criteria may be used based on expected respiratory system parameter values for the given type of patient, e.g. setting an upper limit on these parameter values above which they are no longer physiological plausible. In some embodiments, the SOE (which can be more difficult to detect compared with the SOI) may not be used in the validity (physiological plausibility) assessment. For example, the time point (SOE(n)+d) can instead be defined as a fixed fraction of the breath interval SOE(n):SOE(n+1) extending backward in time from SOE(n+1), e.g. using (SOI(n+1)−F): SOI(n+1)−1 where F is the fixed fraction so that SOE is not needed. Furthermore, the current ventilator settings, such as the pressure support level, can also be used to refine the criteria.

With continuing reference to FIG. 2, if the parameter estimates output by the asynchronous sliding time window respiratory parameters estimator 50 are determined to be valid data by the validator 60, then these estimates are output in an output operation 62, e.g. displayed on the patient monitor 36 and/or the ventilator display 40, time-integrated by WoB or PoB calculator 38 to compute work or power of breathing, used for ventilator control, stored in the patient's Electronic Medical (or Health) Record, or so forth.

On the other hand, if the parameter estimates output by the asynchronous sliding time window respiratory parameters estimator 50 are determined to be invalid data (i.e. physically implausible data) by the validator 60, then process flow passes to a synchronous, i.e. per-breath $P_{mus}(t)$ estimator 70 which estimates $P_{mus}(t)$ and the respiratory system parameters on a per-breath basis, taking into account the physiologically expected shape or profile of $P_{mus}(t)$ over the waveform. For the per-breath parameters estimator 70, each breath identified by the breathing cycle detector 44 is denoted here as a time interval [0, $T_{tot}$] where time 0 corresponds to the first sample at the onset of the inspiration period (i.e. SOI(n) using the notation of the validation criteria C1, C2) and time $T_{tot}$ corresponds to the end of the breath, that is, the last sample just before the beginning of the next breath (i.e. SOI(n+1)−1 using the notation of the validation criteria C1, C2). Note that the illustrative synchronous respiratory parameters estimator 70 uses SOI to delineate a breath interval, but does not use SOE. The synchronous per-breath estimation approaches disclosed herein leverage known physiological constraints on the motion of the lungs by fitting the measured ($P_{aw}(t)$, $\dot{V}(t)$, $V(t)$) samples over a single breath using a single-breath parameterized profile representation of the respiratory muscle pressure $P_{mus}(t)$. The resulting problem is a linear problem that can be solved by techniques such as gradient descent, Marquardt-Levenberg, or similar least squares optimization. Parameters that would introduce non-linearity into the optimization problem (e.g. transition times of the profile) can also be incorporated into the profile, but these parameters are optimized using a grid search. Furthermore, the single-breath parameterized respiratory muscle pressure profile can absorb the baseline pressure $P_{baseline}$ of the Equation of Motion of the Lungs (Equation (2)). To accommodate the possibility of a gradual drift of $P_{baseline}$ over the breath, the illustrative single-breath parameterized respiratory muscle pressure profiles disclosed herein include different effective baseline values $P_0$ and $P_e$ at the beginning and end of the breath intake, respectfully. The resulting modified Equation of Motion of the Lungs can be written as:

$$P_{aw}(t) = R_{rs}\dot{V}(t) + \left(\frac{1}{C_{rs}}\right)V(t) + [P_{mus,profile}(t, P_0, P_p, P_e)]_{T_p, T_e} \quad (7)$$

where $P_{mus,profile}(t, P_0, P_p, P_e)$ is the single-breath parameterized respiratory muscle pressure profile. The least squares optimization optimizes the pressure parameters $P_0$, $P_p$, $P_e$. These pressure parameters are the baseline pressure $P_0$ at the beginning of the breath intake, the maximum negative pressure $P_p$ reached during the breath intake, and the baseline pressure $P_e$ at the end of the breath intake. Typically, $P_0 \cong P_e$ is expected, but some difference between these values may be obtained by the least squares fitting, which accounts for any gradual drift in the baseline pressure $P_{baseline}$ of Equation (2) over time. The notation [ ... ]$T_p,T_e$ denotes that Equation (3) is evaluated with fixed values for time parameters $T_p$ and $T_e$. The time parameter $T_p$ is the time at which the profile reaches the peak negative pressure $P_p$, and the time parameter $T_e$ is the time at which the profile returns to the baseline pressure $P_e$. Incorporating the time parameters $T_p$ and $T_e$ into the least squares fit would result in a non-linear problem which is much more computationally difficult to solve. Accordingly, in illustrative examples herein the time parameters $T_p$ and $T_e$ are fitted using a grid search, that is, Equation (3) is optimized for several possible $(T_p, T_e)$ pairs and the optimization yielding the best fit to the measured ($P_{aw}(t)$, $\dot{V}(t)$) samples over the fitted breath are selected. The least squares fit of Equation (7) to the measured ($P_{aw}(t)$, $\dot{V}(t)$, $V(t)$) samples over the fitted breath entails fitting five parameters: $R_{rs}$, $C_{rs}$, $P_0$, $P_p$, and $P_e$. If the sampling rate is one sample every 10 milliseconds and the breath is of duration 3 seconds, the single-breath data set includes N=300 samples, so that the problem is highly overdetermined. Rapid convergence is facilitated by employing physically realistic starting values for the parameters—for example some suitable starting parameters may be $P_0=P_e=0$ or $P_0=P_e=P_{avg}$ where $P_{avg}$ is the average pressure during the expiration phase. Suitable starting values for the remaining parameters may, for example, be chosen as typical literature values for the type of patient being monitored. Because this five-parameter fit is fast, it is feasible to repeat the optimization for several possible $(T_p, T_e)$ pairs in the time frame of a single breath (typically 3-5 seconds per breath for a healthy adult with a respiration rate in the range 12-20 breaths per second) and select the optimization with the lowest fitting error. Thus, the output latency is on the order of a single breath or less, i.e. 5 seconds or less in some embodiments, making it feasible to execute the estimator 70 after failed validation of the output of the asynchronous estimator 50 while introducing time latency of about one breath or less in the estimated $P_{mus}(t)$ data stream.

Figure 3:
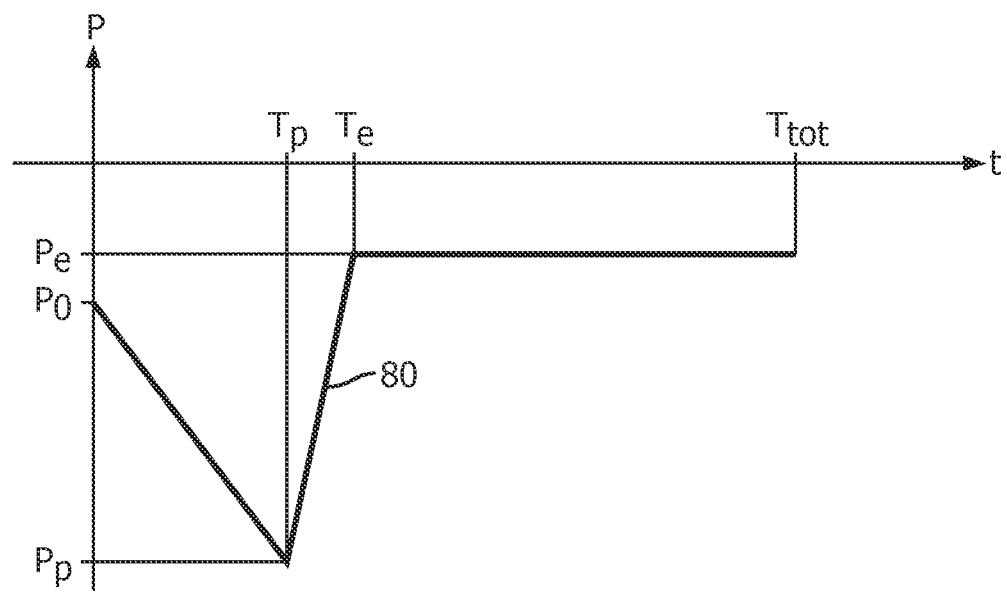
FIGS. 3 and 4 plot two illustrative single-breath piecewise linear (FIG. 3) or piecewise parabolic (FIG. 4) parameterized respiratory muscle pressure versus time breath profile that may be used in the synchronous or "per-breath" estimator of FIG. 2.
Figure 4:
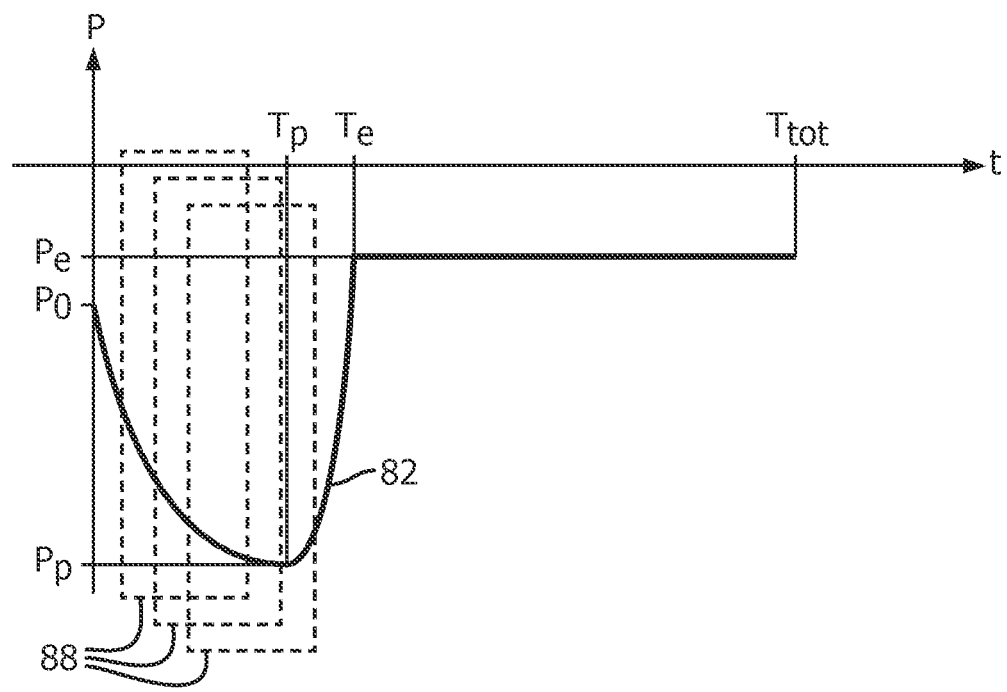

With reference to FIGS. 3 and 4, two illustrative single-breath respiratory muscle pressure waveforms are described. A single-breath piece-wise linear parameterized respiratory muscle pressure profile 80 is illustrated in FIG. 3 and given below:

$$P_{mus,profile}(t) = \begin{cases} P_0\left(1 - \frac{t}{T_p}\right) + P_p\left(\frac{t}{T_p}\right) & \text{for } 0 \leq t < T_p \\ P_p\left(1 - \frac{t - T_p}{T_e - T_p}\right) + P_p\left(\frac{t}{T_p}\right) & \text{for } T_p \leq t < T_e \\ P_e & \text{for } T_e \leq t \leq T_{tot} \end{cases} \quad (8)$$

In this illustrative single-breath parameterized respiratory muscle pressure profile 80, the time parameters $T_p$ and $T_e$ are assumed to be known, and the profile assumes that $P_{mus}(t)$ linearly decreases between t=0 and t=$T_p$, linearly increase between t=$T_p$ and t=$T_e$, and stays constant from t=$T_e$ to t=$T_{tot}$. Applying the Equation of Motion of the Lungs of Equation (3) using the respiratory muscle pressure profile $P_{mus,profile}(t, P_0, P_p, P_e)$ of Equation (4) (where again $T_p$ and $T_e$ are taken as fixed values) to a set of measurement samples ($P_{aw}(0)$, $\dot{V}(0)$, $V(0)$), ($P_{aw}(1)$, $\dot{V}(1)$, $V(1)$), . . . , ($P_{aw}(T_{tot})$, $\dot{V}(T_{tot})$, $V(T_{tot})$) over a single breath yields the following matrix equation:

$$\begin{bmatrix} P_Y(0) \\ \vdots \\ P_Y(T_p - 1) \\ P_Y(T_p) \\ \vdots \\ P_Y(T_e - 1) \\ P_Y(T_e) \\ \vdots \\ P_Y(T_{tot}) \end{bmatrix} = \quad (9)$$

$$\begin{bmatrix} \dot{V}(0) & V(0) & \left(1-\dfrac{0}{T_p}\right) & \dfrac{0}{T_p} & 0 \\ \vdots & \vdots & \vdots & \vdots & \vdots \\ \dot{V}(T_p-1) & V(T_p-1) & \left(1-\dfrac{T_p-1}{T_p}\right) & \dfrac{T_p-1}{T_p} & 0 \\ \dot{V}(T_p) & V(T_p) & 0 & \left(1-\dfrac{0}{T_e-T_p}\right) & 1 \\ \vdots & \vdots & & \vdots & \\ & & & \left(\dfrac{T_e-1-T_p}{T_e-T_p}\right) & \\ \dot{V}(T_e-1) & V(T_e-1) & \vdots & 1-\dfrac{T_p}{T_e-T_p} & \vdots \\ \dot{V}(T_e) & V(T_e) & \vdots & 0 & \vdots \\ \vdots & \vdots & & \vdots & \\ \dot{V}(T_{tot}) & V(T_{tot}) & 0 & 0 & 1 \end{bmatrix} \begin{bmatrix} R \\ E \\ P_0 \\ P_p \\ P_e \end{bmatrix}$$

where in Equation (9) the notation $P_Y$ replaces the airway pressure notation $P_{aw}$ used elsewhere herein (the subscript "Y" indicating the illustrative use of a Y-piece as the patient accessory 18), and respiratory system resistance $R_{rs}$ and elastance $E_{rs}$ are represented by the shortened forms R and E, respectively. Matrix Equation (9) is solved for the parameters vector $[R\ E\ P_0\ P_p\ P_e]^T$ using least squares optimization (e.g. gradient descent, Levenberg-Marquardt, etc), and the respiratory muscle pressure is estimated over the breath interval $[0,\ T_{tot}]$ using Equation (8) with the optimized values for $P_0$, $P_p$, and $P_e$ and the assumed fixed values for $T_p$ and $T_e$.

Equation (9) is advantageously a linear problem that can be expressed in the form $\overline{Y}=M\overline{X}$ where $\overline{Y}$ is a measurements vector (more particularly, the airway pressure data vector $\overline{P}_{aw}=[P_{aw}(0)\ P_{aw}(1)\ \ldots\ P_{aw}(T_{tot})]^T$ in Equation (9)), $\overline{X}$ is a parameters vector (more particularly, the parameters vector $[R\ E\ P_0\ P_p\ P_e]^T$ in Equation (9)), and M is a connecting matrix. Optimizing parameters $T_p$ and $T_e$ as part of the least squares optimization would make the problem non-linear and not expressible in the form $\overline{Y}=M\overline{X}$. Thus, in some embodiments no time parameters of the respiratory muscle pressure profile are fitted by the least squares fitting; rather, optimization of $T_p$ and $T_e$ is performed by way of a grid search, in which Equation (9) is solved for several different choices of $T_p$ and $T_e$ and the values of $T_p$ and $T_e$ for the best optimization result are chosen. This involves only two parameters $T_p$ and $T_e$, and moreover these parameters have a narrow range of physiologically plausible values. For example, in selecting values for the grid search, the condition $0<T_p<T_e<T_{tot}$ holds, and these constraints can be further narrowed by taking into account the physiologically plausible range of the inspiration period over the breath interval $[0, T_{tot}]$.

With continuing reference to FIG. 3 and with further reference to FIG. 4, to provide further improvement in the per-breath respiratory parameters estimation, the least squares optimization can also be repeated for two or more different respiratory muscle pressure profile shapes, and the best optimization (that is, the optimization with the lowest fitting error) is chosen. By way of further non-limiting illustration, FIG. 4 illustrates a single-breath piece-wise parabolic parameterized respiratory muscle pressure profile 82 in which the interval $[0, T_p)$ is a decreasing parabolic function starting at $P_0$ and ending at $P_p$, the interval $[T_p, T_e)$ is an increasing parabolic function starting at $P_p$ and ending at $P_e$, and the interval $[T_e, T_{tot}]$ has constant value $P_e$. The time parameters $T_p$ and $T_e$ are again assumed to be known, and can be optimized using a grid search. The least squares optimization can also be repeated for different instances of the single-breath parabolic parameterized respiratory muscle pressure profile 82 having different bowing parameters for the two parabolic segments $[0, T_p)$ and $[T_n, T_e)$. Because each least squares minimization with a given profile shape and set of time parameters $T_p$ and $T_e$ is a linear problem of the form $\overline{Y}=M\overline{X}$, a relatively large number of such optimizations (e.g. a dozen or more) can be performed in 1-2 seconds, so that the overall optimization can be completed in the time frame of a single breath.

In some more generalized profile embodiments, the single-breath piece-wise parameterized respiratory muscle pressure profile has a general shape which includes a downward portion extending from an initial pressure ($P_0$) at the beginning of the breath interval (time t=0) to a negative pressure of largest magnitude ($P_p$) at a first time $T_p$, an upward portion extending from the first time $T_p$ to a second time $T_e$, and a flat portion extending from the second time $T_e$ to the end of the breath interval. This general shape encompasses the shapes of profiles 80, 82 of FIGS. 3 and 4, as well as numerous variant (for example, having a parabolic shape between t=0 and t=$T_p$ and a linear shape between t=$T_p$ and t=$T_e$).

With particular reference to FIG. 4, for comparative illustration some successive sliding (or moving) time windows 88 are shown in dotted lines, to illustrate a typical time duration of the sliding window used by the asynchronous sliding time window respiratory parameters estimator 50. As indicated in FIG. 4, the sliding time window as a size (i.e. time interval) that is less than the time interval of a single breath, and in some preferred embodiments is less than one-third of the breath interval. The asynchronous sliding time window respiratory parameters estimator 50 performs the estimations (e.g. Equations (3) and (4)) within the relatively narrow time window 88 without reference to where this time window 88 is located within the breath cycle (i.e. asynchronously); whereas, the per-breath respiratory parameters estimator 70 fits Equation (9) over the entire breath interval $[0, T_{tot})$ with the interval situated to encompass a single breath from start of inspiration (SOI) to end of expiration (i.e. just before SOI of the next breath).

In sum, using the linear and parabolic profiles of FIGS. 3 and 4, respectively, the per-breath respiratory parameters estimation can be performed by the estimator 70 of FIG. 2 as follows: (1) define a set of time pairs $(T_p, T_e)$; (2) for each pair, construct the corresponding least squares optimization problem with piecewise linear and piecewise parabolic profiles (two optimization problems are constructed for each time pair, one using the piecewise linear profile of FIG. 3 and the other using the piecewise quadratic profile of FIG. 4); (3) solve each least squares optimization problem and compute the corresponding sum-of-squares; (4) find the minimum sum-of-squares among all the least squares optimizations; and (5) use the parameters vector $[R\ E\ P_0\ P_p\ P_e]^T$ and the appropriate profile $P_{mus,profile}(t)$ for the solution with the minimum sum-of-squares to compute to estimate $P_{mus}(t)$ and the respiratory system resistance and elastance for the breath.

The illustrative estimators 50, 70 are constructed to evaluate the first-order Equation of Motion of the Lungs of Equation (2). However, variant models of the motion of the lungs may be used in one or both of the estimators 50, 70, such as a second-order Equation of Motion of the Lungs:

$$P_{aw}(t) = L\ddot{V}(t) + (R_0 + R_1|\dot{V}(t)|)\dot{V}(t) + EV(t) + P_{mus}(t) + P_{baseline} \quad (10)$$

which includes four respiratory system parameters: a parameter L representing respiratory system inertance, two resistance parameters $R_0$ and $R_1$ (which replace the single resistance $R_{rc}$ of Equation (2) and characterize a parabolic resistance variation with flow rate), and an elastance E (or equivalent compliance term 1/C) equivalent to its analog in the first-order Equation of Motion of the Lungs of Equation (2). The Equation of Motion of the Lungs of Equation (6) is therefore an equivalent LRC circuit. By way of illustration, the matrix Equation (9) is readily modified to include the additional parameters of the second-order model of Equation (10).

With returning reference to FIG. 2, the respiratory parameter values $P_{mus}(t)$, $R_{rs}(t)$ and $E_{rs}(t)$ or $C_{rs}(t)$ output by the per-breath respiratory parameters estimator 70 are evaluated as to physiological plausibility by the validator 60 which again operates on a per-breath basis using the SOI and SOE delineations detected by the breathing cycle detector 44. The validator 60 may apply the same illustrative validation criteria C1 and C2 as was described previously for validating the asynchronous estimates. Alternatively, since the per-breath estimator 70 outputs $P_{mus}(t)$ represented by the fitted profile $P_{mus,profile}(t)$, the validation can operate on the fitted parameters $P_0$, $P_p$, $P_e$. For example, a suitable validation criterion may be $P_p < P_{Th}$ where $P_{Th}$ is a non-negative threshold that can be a function of the current pressure support level (note that $P_p$ is expected to be a negative pressure). If the parameter estimates output by the per-breath respiratory parameters estimator 70 are determined to be valid data by the validator 60, then these estimates are output in the output operation 62 for the breath, while the invalid data that was output for the breath by the asynchronous respiratory parameters estimator 50 are discarded. Meanwhile, the asynchronous respiratory parameters estimator 50 continually operates (i.e. for each successive position of the sliding window 88) to generate asynchronous estimation data until the next breath is complete and the process repeats with validation of the estimates from the asynchronous respiratory parameters estimator 50 and, if found invalid, repeated invocation of the per-breath respiratory parameters estimator 70.

If, for a particular breath, the validator 60 finds that the parameters estimated by the asynchronous respiratory parameters estimator 50 are invalid and further finds that the parameters subsequently estimated by the per-breath respiratory parameters estimator 70 are also invalid, then various further actions can be taken. In the approach of illustrative FIG. 2, a further estimation attempt is made by an estimator with no spontaneous breathing 72 in which $P_{mus}(t)$ is set to zero. With $P_{mus}(t)=0$ Equation (2) reduces to:

$$P_{aw}(t) = R_{rs}\dot{V}(t) + \left(\frac{1}{C_{rs}}\right)V(t) + P_{baseline} \quad (11)$$

The estimator with no spontaneous breathing 72 thus performs a least squares optimization with the three fitted parameters being $R_{rs}$, $C_{rs}$, and $P_{baseline}$. This can be done either synchronously, e.g. over the single-breath data set [0, $T_{tot}$) same as the synchronous estimator 70, or the fit can be done asynchronously, e.g. using the sliding window paradigm of the asynchronous estimator 50. The resulting estimates assuming no spontaneous breathing are again assessed by the validator 60 to determine whether the data are valid. The estimator with no spontaneous breathing 72 assumes $P_{mus}(t)=0$, and so the validator 60 in this case only determines whether the fitted values for $R_{rs}$, $C_{rs}$, and (optionally) $P_{baseline}$ are physiologically plausible. If so, then these estimates are output in the output operation 62 for the breath, while the invalid data that were output for the breath by the asynchronous respiratory parameters estimator 50 and the per-breath estimator 70 are both discarded. Optionally, an audible and/or visual warning is issued indicating that the respiratory parameters estimator/validator 30 has detected that the patient is no longer spontaneously breathing. (This alarm might not be issued unless this condition is detected over some minimum number of successive breaths to reduce the potential for a false alarm. Conversely, the alarm could additionally/alternatively be designed to provide an alert if the respiratory parameters estimator/validator 30 detects a non-zero $P_{mus}(t)$ in a patient who was previously not spontaneously breathing.)

With continuing reference to FIG. 1, if the validator 60 still further finds that the estimates output by the estimator 72 with $P_{mus}(t)=0$ set are still invalid, then a further remedial action 90 is taken for the breath, such as issuing null data or (in the illustrative example) outputting a repetition of the data from the last validated breath, preferably with a warning that these data are unreliable. (Again, the warning might not be issued unless this condition is detected over some minimum number of successive breaths to reduce the potential for a false alarm).

In the illustrative embodiments, the asynchronous respiratory parameters estimator 50 is applied first, and the synchronous respiratory parameters estimator 70 is then applied only if the asynchronously estimated respiratory parameters fail to validate. This approach advantageously leverages the small window size of the asynchronous sliding window, which enables the asynchronous respiratory parameters estimator 50 to be estimating the parameters essentially continuously as airway pressure and flow rate data are being acquired for a breath that is currently being executed by the patient. The latency is only on the order of the sliding window time duration (i.e. window width) which is a small fraction of the breath interval as diagrammatically indicated by the illustrative successive (sliding) time windows 88 in FIG. 4.

However, it is alternatively contemplated to apply the synchronous respiratory parameters estimator 70 first and to validate the synchronously estimated respiratory parameters, and to then apply the asynchronous respiratory parameters estimator 50 only if the synchronously estimated parameters fail to validate. This approach might be appropriate if, for example, the synchronous respiratory parameters estimator 70 is expected to provide more accurate estimates for a given patient.

As a further variant, it is contemplated to apply both the asynchronous respiratory parameters estimator 50 and the synchronous respiratory parameters estimator 70, and to select either the asynchronous or synchronous estimates based on a selection criterion. In such embodiments, if both asynchronous and synchronous estimates validate then it is contemplated to average or otherwise combine the asynchronous and synchronous estimates.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A respiratory monitor device comprising:
an airway pressure sensor configured to acquire airway pressure data as a function of time and an airway flow sensor configured to acquire airway flow data as a function of time;
a breathing cycle detector comprising an electronic processor programmed to detect a breath interval bounded by successive start of inspiration (SOI) events in at least one of the airway pressure data and the airway flow data; and
a respiratory parameters estimator and validator comprising an electronic processor programmed to perform operations including:
fitting the airway pressure and airway flow data to an equation of motion of lungs relating airway pressure and airway flow to generate estimated respiratory parameters for the breath interval, the fitting being performed in a sliding time window of fixed duration and that is not synchronized with the breath interval by not being aligned with any particular interval of the breath interval;
performing validation of the estimated respiratory parameters for the breath interval using at least one physiological plausibility criterion; and
responsive to failure of the validation of the estimated respiratory parameters for the breath interval, re-fitting the airway pressure and airway flow data to the equation of motion of the lungs to generate refitted estimated respiratory parameters for the breath interval, the re-fitting being performed in a time window that is equal to the breath interval; and
a mechanical ventilator configured to deliver ventilation therapy to a patient using the generated estimated respiratory parameters or refitted estimated respiratory parameters for the breath interval.

2. The respiratory monitor device of claim 1 wherein the fitting includes:
one or more first fittings that generate an estimated respiratory system resistance and an estimated respiratory system compliance or elastance; and
a second fitting in which the estimated respiratory system resistance and the estimated respiratory system compliance or elastance are held constant and the second fitting generates an estimated respiratory muscle pressure.

3. The respiratory monitor device of claim 1 wherein the re-fitting comprises:
re-fitting the airway pressure and airway flow data to the equation of motion of the lungs relating airway pressure, airway flow, and a single-breath parameterized respiratory muscle pressure profile aligned with the SOI of the breath interval to generate the refitted estimated respiratory parameters for the breath interval.

4. The respiratory monitor device of claim 3 wherein the single-breath parameterized respiratory muscle pressure profile is $P_{mus,profile}(t, P_0, P_p, P_e)$, where $P_0$ is a fitted parameter representing respiratory muscle pressure at the beginning of the breath interval, $P_p$ is a fitted parameter representing a negative respiratory muscle pressure of maximum magnitude over the breath interval, and $P_e$ is a fitted parameter representing respiratory muscle pressure at the end of the breath interval.

5. The respiratory monitor device of claim 1 wherein the estimated respiratory parameters or the refitted estimated respiratory parameters include a respiratory muscle pressure, a respiratory system resistance, and at least one of (i) a respiratory system elastance and (ii) a respiratory system compliance.

6. The respiratory monitor device of claim 1 wherein the respiratory parameters estimator and validator is programmed to perform operations further including:
performing validation of the refitted estimated respiratory parameters for the breath interval using at least one physiological plausibility criterion defined with respect to the breath interval; and
responsive to failure of the validation of the refitted estimated respiratory parameters for the breath interval, fitting the airway pressure and airway flow data to the equation of motion of the lungs with a respiratory muscle pressure set equal to zero to estimated respiratory parameters with no spontaneous breathing for the breath interval.

7. The respiratory monitor device of claim 1 wherein the estimated respiratory parameters or the refitted estimated respiratory parameters include respiratory muscle pressure and the respiratory monitor device further comprises:
a work or power of breathing estimator comprising an electronic processor programmed to estimate a power of breathing (PoB) or work of breathing (WoB) by time-integration of the respiratory muscle pressure for the breath interval;
wherein the PoB or WoB is displayed on a display component of the mechanical ventilator.

8. The respiratory monitor device of claim 1 wherein the breathing cycle detector is further programmed to detect start of expiration (SOE) in the breath interval bounded by successive start of inspiration (SOI) events, and the at least one physiological plausibility criterion defined with respect to the breath interval includes:
a physiological plausibility criterion comparing respiratory muscle pressure during inspiration and respiratory muscle pressure during expiration.

9. The respiratory monitor device of claim 1 wherein the breathing cycle detector is further programmed to detect start of expiration (SOE) in the breath interval bounded by successive start of inspiration (SOI) events, and the at least one physiological plausibility criterion defined with respect to the breath interval includes:
a physiological plausibility criterion comparing respiratory muscle pressure at SOE and respiratory muscle pressure during expiration.

10. The respiratory monitor device of claim 1 wherein the estimated respiratory parameters or the refitted estimated respiratory parameters include respiratory muscle pressure and the respiratory monitor device further comprises:
a work or power of breathing estimator comprising an electronic processor programmed to estimate a power of breathing (PoB) or work of breathing (WoB) by time-integration of the respiratory muscle pressure for the breath interval;
wherein the PoB or WoB is used as a control input by the mechanical ventilator.

11. A non-transitory storage medium storing instructions executable by an electronic processor to perform a respiratory parameters estimation method operating on airway pressure data and airway flow data, the method including:
detecting a breath interval bounded by successive start of inspiration (SOI) events in at least one of the airway pressure data and the airway flow data;

fitting the airway pressure and airway flow data to an equation of motion of the lungs relating airway pressure and airway flow to generate estimated respiratory parameters for the breath interval, the fitting being performed using one of a sliding time window of fixed duration and that is not synchronized with the breath interval by not being aligned with any particular time interval of the breath interval and a single-breath parameterized respiratory muscle pressure profile that corresponds to the SOI of the breath interval;

performing validation of the estimated respiratory parameters for the breath interval using at least one physiological plausibility criterion defined with respect to the breath interval; and responsive to failure of the validation of the estimated respiratory parameters for the breath interval, re-fitting the airway pressure and airway flow data to the equation of motion of the lungs to generate re-estimated respiratory parameters for the breath interval using the other of the sliding time window that is not synchronized with the breath interval and the single-breath parameterized respiratory muscle pressure profile that corresponds to the SOI of the breath interval; and controlling a mechanical ventilator to deliver ventilation therapy to a patient using the generated estimated respiratory parameters or the re-estimated respiratory parameters for the breath interval.

12. The non-transitory storage medium of claim 11 wherein the method further includes:

performing validation of the re-estimated respiratory parameters for the breath interval using at least one physiological plausibility criterion defined with respect to the breath interval; and responsive to failure of the validation of the re-estimated respiratory parameters for the breath interval, fitting the airway pressure and airway flow data to the equation of motion of the lungs with a respiratory muscle pressure set equal to zero to estimate respiratory parameters with no spontaneous breathing for the breath interval.

13. The non-transitory storage medium of claim 11 wherein the method further includes:

detecting start of expiration (SOE) in the breath interval bounded by successive start of inspiration (SOI) events;

wherein the at least one physiological plausibility criterion defined with respect to the breath interval includes at least one of:

a physiological plausibility criterion comparing respiratory muscle pressure during inspiration and respiratory muscle pressure during expiration; and a physiological plausibility criterion comparing respiratory muscle pressure at SOE and respiratory muscle pressure during expiration.

14. The non-transitory storage medium of claim 11, wherein the estimated respiratory parameters or the re-estimated respiratory parameters include respiratory muscle pressure and the method further comprises:

estimating a power of breathing (PoB) or work of breathing (WoB) by time-integration of the respiratory muscle pressure for the breath interval; and displaying the PoB or WoB on a display component of the mechanical ventilator.

15. The non-transitory storage medium of claim 11, wherein the estimated respiratory parameters or the re-estimated respiratory parameters include respiratory muscle pressure and the method further comprises:

estimating a power of breathing (PoB) or work of breathing (WoB) by time-integration of the respiratory muscle pressure for the breath interval; and controlling the mechanical ventilator to deliver ventilation therapy to the patient with the estimated PoB or WoB.

16. A respiratory parameters estimation method comprising:

acquiring airway pressure data using an airway pressure sensor, acquiring airway flow data using an airway flow sensor, detecting a breath interval bounded by successive start of inspiration (SOI) events in at least one of the airway pressure data and airway flow data;

fitting the airway pressure and airway flow data to an equation of motion of lungs relating airway pressure and airway flow to generate estimated respiratory parameters for the breath interval, the fitting being performed using one of a first fitting in a sliding time window of fixed duration that is not synchronized with the breath interval by not being aligned with any particular time interval of the breath interval, and a second fitting in a time window that is equal to the breath interval;

performing a validating process for the estimated respiratory parameters for the breath interval; and determining that the validating process is unsuccessful, re-fitting the airway pressure and airway flow data to the equation of motion of the lungs to generate re-estimated respiratory parameters for the breath interval using the other of the first fitting in the sliding time window that is not synchronized with the breath interval, and the second fitting in the time window that is equal to the breath interval;

via a mechanical ventilator, delivering ventilation therapy to a patient using the generated re-estimated respiratory parameters for the breath interval.

17. The respiratory parameters estimation method of claim 16 further comprising:

performing a second validating process on the re-estimated respiratory parameters for the breath interval; and determining that the second validating process of the re-estimated respiratory parameters is unsuccessful, and fitting the airway pressure and airway flow data to the equation of motion of the lungs with respiratory muscle pressure set to zero to generate additional estimated respiratory parameters for the breath interval without spontaneous breathing.

18. The respiratory parameters estimation method of claim 16 wherein the validating process uses at least one physiological plausibility criterion.

19. The respiratory parameters estimation method of claim 16, wherein the estimated respiratory parameters and the re-estimated respiratory parameters include respiratory muscle pressure and the method further comprises:

estimating a power of breathing (PoB) or work of breathing (WoB) by time-integration of the respiratory muscle pressure for the breath interval; and displaying the PoB or WoB on a display component of the mechanical ventilator.

20. The respiratory parameters estimation method of claim 16, wherein the estimated respiratory parameters and the re-estimated respiratory parameters include respiratory muscle pressure and the method further comprises:

estimating a power of breathing (PoB) or work of breathing (WoB) by time-integration of the respiratory muscle pressure for the breath interval; and controlling the mechanical ventilator to deliver ventilation therapy to the patient with the estimated PoB or WoB.

* * * * *